(12) United States Patent
Globus et al.

(10) Patent No.: US 10,287,635 B2
(45) Date of Patent: May 14, 2019

(54) MICRO-RNA BASED DIAGNOSES OF OVARIAN AND OTHER CANCERS VIA SUB-TERAHERTZ VIBRATIONAL SPECTROSCOPY

(71) Applicant: Vibratess, LLC, Charlottesville, VA (US)

(72) Inventors: Tatiana Globus, Charlottesville, VA (US); Boris Gelmont, Charlottesville, VA (US); Amir Jazaery, Houston, TX (US); Alexei Bykhovski, Cary, NC (US); Igor Sizov, Alexandria, VA (US); Aaron Moyer, Ruckersville, VA (US); Jerome Ferrance, Charlottesville, VA (US)

( * ) Notice: Subject to any disclaimer, the term of this patent is extended or adjusted under 35 U.S.C. 154(b) by 0 days.

(21) Appl. No.: 15/435,111

(22) Filed: Feb. 16, 2017

(65) Prior Publication Data

US 2017/0247764 A1     Aug. 31, 2017

Related U.S. Application Data

(60) Provisional application No. 62/295,953, filed on Feb. 16, 2016.

(51) Int. Cl.
  *C12Q 1/68*   (2018.01)
  *C12Q 1/6886* (2018.01)

(52) U.S. Cl.
  CPC ..... *C12Q 1/6886* (2013.01); *C12Q 2600/158* (2013.01); *C12Q 2600/178* (2013.01)

(58) Field of Classification Search
  CPC ............ C12Q 1/6886; C12Q 2600/158; C12Q 2600/178
  See application file for complete search history.

(56) References Cited

U.S. PATENT DOCUMENTS

| | | | |
|---|---|---|---|
| 6,887,711 B1 * | 5/2005 | Diem ................. | G01N 15/1456 436/164 |
| 2005/0203578 A1 * | 9/2005 | Weiner ..................... | A61N 5/00 607/2 |
| 2014/0070102 A1 * | 3/2014 | Globus .............. | G01N 21/3586 250/339.07 |
| 2015/0005188 A1 * | 1/2015 | Levner ................. | C12Q 1/6804 506/9 |

\* cited by examiner

*Primary Examiner* — Mark R Gaworecki
(74) *Attorney, Agent, or Firm* — Dale Jensen, PLC; Dale Jensen

(57) ABSTRACT

Certain exemplary embodiments can provide a method, which comprises causing a determination to be made that a body fluid sample is from a patient with cancer. The determination can be made via analyzing the body fluid sample by sub-THz resonance spectroscopy with absorption determinations being made at a plurality of frequencies between 0.05 and 1.0 THz to show a presence of specific MicroRNAs as cancer related molecules in the body fluid.

9 Claims, 17 Drawing Sheets
(13 of 17 Drawing Sheet(s) Filed in Color)

| Sample | Type | Concentration, cells/μl |
|---|---|---|
| JS-150 (S-line) Type II | Cancer | 150 |
| JS-300 (S-line) Type II | Cancer | 300 |
| JE-150 (E-line) Type I | Cancer | 150 |
| JE-300 (E-line) Type I | Cancer | 300 |
| JN-9, line FT131 | Normal | 100 |
| JN-2, line FT131 | Normal | 50 |

FIG. 1B

| Name | Sequence | Entry in the database |
|---|---|---|
| mir-200a (22bp) | CAUCUUACCGGACAGUGC | MI0000737 |
| mir-200b (22bp) | UAAUACUGCCUGGUAAUG | MI0000342 |
| mir-200c (22bp) | CGUCUUACCCAGCAGUGU | MI0000650 |
| mir-141 (22bp) | UAACACUGUCUGGUAAAG | MI0000457 |

FIG. 7C

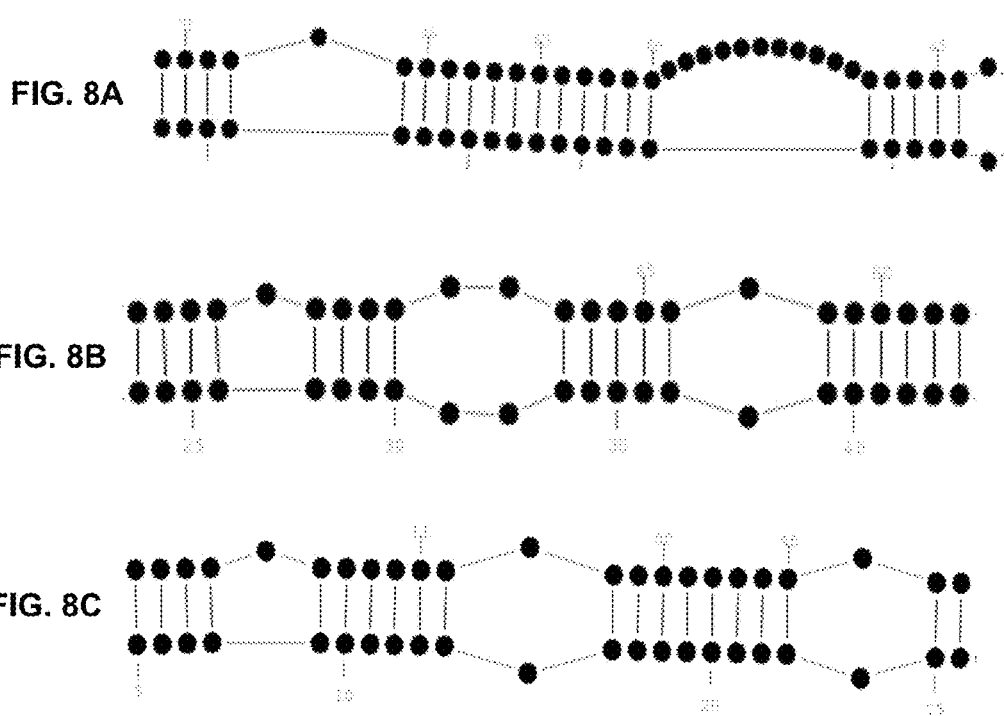
FIGS. 8A, 8B, and 8C

MICRO-RNA BASED DIAGNOSES OF OVARIAN AND OTHER CANCERS VIA SUB-TERAHERTZ VIBRATIONAL SPECTROSCOPY

CROSS-REFERENCES TO RELATED APPLICATIONS

This application claims priority to, and incorporates by reference herein in its entirety, U.S. Provisional Patent Application Ser. No. 62/295,953, filed Feb. 16, 2016.

BRIEF DESCRIPTION OF THE DRAWINGS

The patent or application file contains at least one drawing executed in color. Copies of this patent or patent application publication with color drawings will be provided by the office upon request and payment of the necessary fee. A wide variety of potential practical and useful embodiments will be more readily understood through the following detailed description of certain exemplary embodiments, with reference to the accompanying exemplary drawings in which:

FIG. 1B a table of samples of cells fixed in 70% ethanol that were tested;

FIG. 7C a table of studied miRNAs;

FIGS. 8A, 8B, and 8C show human microRNA duplex models, miR-200a, 200b and 200c after maturation (without loop but with mismatches);

DETAILED DESCRIPTION

Figure 1:
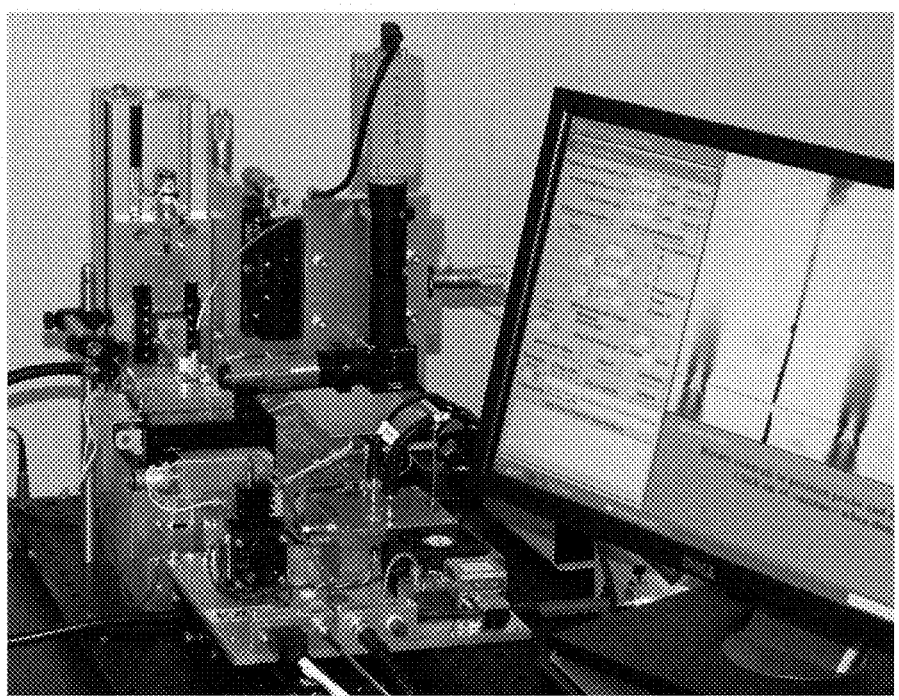
FIG. 1 an exemplary sub-THz spectrometer with high spectral and spatial resolution for bio-identification.

Certain exemplary embodiments can provide a method, which comprises causing a determination to be made that a body fluid sample is from a patient with cancer. The determination can be made via analyzing the body fluid sample by sub-THz resonance spectroscopy with absorption determinations being made at a plurality of frequencies between 0.05 and 1.0 THz to show the presence of specific Micro-RNAs as cancer related molecules in the body fluid.

Certain exemplary embodiments provide novel sub-terahertz ("sub-THz") resonance spectroscopy combined with molecular dynamics ("MD") computation as a promising approach for analysis and quantification of known potential molecular biomarkers in ovarian ("OC") cancer cells and body liquids. The ability of sub-THz spectroscopy to identify and quantify biological molecules is demonstrated by interrogation of resonance features caused by atomic vibrations within biological molecules in cancer and normal samples. In vitro human cell cultures of two ovarian cancer subtypes, SK-OV-3 human epithelial and ES-2 human clear cell carcinoma, were characterized in comparison with a normal nontransformed cell line (FT131—human fallopian tube epithelial cell line). A dramatic difference between the THz absorption spectra of cancer and normal cells is observed with much higher absorption intensity and a very strong absorption peak at a frequency of approximately 13 cm$^{-1}$ dominating the spectra from cancer samples. Comparison of experimental spectra with MD predictions of spectroscopic signatures suggests that this pronounced spectral peak as well as several other intense features could originate from micro-RNA ("miRNA") molecules specific for OC, particularly the mir-200 family. The less intense regions of the cancer cell spectra are similar to the signatures of normal cells and most probably represent contribution from proteins and molecules that carry genetic information. Even though ovarian cancer is utilized for this proof of concept, the sub-THz spectroscopy method is very general and can be as well applied to other cancer types.

I. Introduction

Epithelial ovarian cancer is the most lethal female reproductive malignancy. Ovarian cancer is a devastating illness in which only approximately 20% of patients are diagnosed with early stage I disease. The main reasons are lack of minimally invasive, early detection tests, subtle symptom development and tumor chemo-resistance. Currently, early detection interventions include serum measurement of protein biomarkers (e.g., CA-125, HE4, OVA1®) (OVA1 is a registered trademark of Vermillion, Inc., 12117 Bee Caves Road, Austin, Tex. 78738) and ultrasound imaging. However, recently a randomized controlled trial of over 78,000 women demonstrated the lack of sensitivity and specificity, and overall benefit of this approach with a documented sensitivity of serum protein biomarker CA-125 for early stage disease of only approximately 40%. In addition, only approximately 10-15% of patients will remain in prolonged remission after initial cytotoxic therapy. At the same time, ovarian cancer is highly curable if detected early (approximately 85% survival for stage I disease). Thus, development of novel approaches for improving the limitations for detection of early stage disease and identification of stable biomarkers, which can be routinely measured in easily accessible samples, remains a high priority area of investigation in gynecological oncology.

Human serum and other body fluids are rich resources for the identification of novel biomarkers, which can be measured in routine clinical diagnosis. Over many decades it has been shown that cell-free DNA and RNA are present in serum and other body fluids and that these circulating nucleic acids may represent potential biomarkers. Recent advances in sequencing technologies have led to an increased focus on blood-derived nucleic acid-based approaches for biomarker discovery. Investigations of differences between normal and malignant cells have revealed alterations in DNA, proteins and associated messenger RNA ("mRNA") changes, as well as, deregulated noncoding RNA expression. Many of these differences have been shown to be detectable in the blood stream. Therefore, there is strong rationale for taking advantage of increasingly available sequencing modalities for blood-derived biomarker discovery.

miRNAs are a novel class of evolutionarily conserved small (18-24 base pair nucleotides) non-coding RNA molecules, which are important regulators of gene expression. Hundreds of miRNAs have been found in various organisms, suggesting their potential roles in all biological events. Expression levels of miRNAs can distinguish malignant and nonmalignant ovarian epithelium. A number of advances suggested that the use of miRNA as a biomarker for disease might be useful, particularly for cancer detection. First, the potential exists to extract and reliably determine cell-free miRNA in body fluids like serum. This makes it possible to evaluate biomarkers using less invasive procedures such as blood draws rather than the need for a biopsy, and could potentially be used to detect disease at an earlier stage in individuals genetically prone to a particular cancer. Second, cell-free miRNAs in body fluids are stable under harsh conditions including boiling, low/high pH, extended storage and multiple freeze-thaw cycles. Serum and other body fluids contain relatively stable microRNA signatures. A good correlation is observed when the individual miRNA levels are compared between serum and plasma samples from the same patient donors, thus, both sample types are suitable for the analysis of cell-free miRNAs. The miRNA abundance profile of bodily fluids reflects physiological and/or pathological conditions and, furthermore, does so more accurately than an mRNA abundance profile. While mRNA can be translated into protein to have a biological effect, miRNAs are, themselves, an active moiety, often influencing the expression of multiple other genes, and thus likely reflecting altered physiology more directly. Thus, the profiles of circulating miRNAs can be used for the identification of novel non-invasive biomarkers. Overall, there is strong rationale for taking advantage of increasingly available sequencing modalities for blood-derived biomarker discovery. Several miRNA signatures that are unique to ovarian cancer have been proposed and a set of highly abundant serum miRNAs has recently been found in patients with ovarian cancer, some of which were also deregulated in patients exhibiting normal CA-125 serum levels. It has also been found that miRNA signatures were different between ovarian carcinoma histotypes (e.g., serous, endometrioid, clear cell, and mucinous). Circulating miRNAs might be good non-invasive markers, which could contribute to improving established clinical diagnostic tests at the early stage.

One of the main problems associated with extracting and analyzing circulating miRNA is quantification of the miRNA. Analysis of serum miRNAs by stem-loop reverse transcription PCR ("RT-PCR") has been used for sensitive detection of low abundant circulating miRNAs with relatively good reproducibility. The extraction of cell-free miRNAs for reliable detection and subsequent miRNA quantification using a TaqMan microRNA assay, or other methods with amplification, are however multi-step time consuming procedures. These methods are costly and typically yield terabytes of data requiring significant bioinformatics analysis capabilities to analyze the data. Thus, certain exemplary embodiments provide a screening test that is based on ubiquitous nucleic acid composition differences between normal and malignant cells, but is simple to perform and interpret. In addition certain exemplary embodiments provide tools, which can help identify the biology involved in cancer development and progression.

Certain exemplary embodiments provide THz spectroscopic techniques and systems having high spectral and spatial resolution, and apply such techniques for quantification of the miRNA in cancer cells and body liquids. We applied combined experimental and computational approaches to investigate the ability of sub-THz spectroscopy to identify and quantify biological molecules. Our initial study using this technique demonstrated spectroscopic signatures from ovarian cancer cells by interrogation of resonance features caused by atomic vibrations within biological molecules, which are absent in normal cells.

Ovarian cancer is used for this first demonstration; however the method is very general and can be as well applied to other cancer types.

II. Sub-THz Vibrational Spectroscopy Technique for Bio-Identification.

THz waves can be extremely important for the life sciences because of the unique capability of this radiation to interact with vibrations of atoms within biological molecules to produce specific molecular fingerprints.

Sub-THz vibrational spectroscopy utilizes wavelengths beyond those traditionally used for chemical and biomolecular analysis. Biological materials are active in the frequency range of approximately 0.05-1 THz (the submillimeter-wave range, approximately 1.5-30 $cm^{-1}$) and above. These frequency and wavelength domains, the spectral range between the upper end of the radio waves and the lowest optical waves has been called the "Terahertz Gap", because so little was known about them and because of the absence of radiation sources and detectors. Absorbance measurements in the THz region are emerging as a new analytical technology.

Low energy THz radiation interacts with the low-frequency internal molecular motions (i.e., vibrations) involving the weakest hydrogen bonds ("H-bonds") and other weak connections within molecules by exciting these vibrations. Although hydrogen bonds are weak and have only approximately 5% of the strength of covalent bonds, multiple hydrogen bonds stabilize the structure of biopolymers, in particular holding the two strands of the DNA double helix together, or holding polypeptides together in different secondary structure conformations. The sub-THz regions of absorption spectra of bio-molecules and species reveal these low frequency molecular motions as resonances. The resonant frequencies of such motions, low energy vibrational modes, are strongly dependent on the three-dimensional molecular structure. As such, these vibrational modes are sensitive to conformational changes of molecules and to environment. The sub-THz vibrational spectroscopy techniques for identifying and characterizing objects are based on the specificity of spectroscopic signatures that reflects absorption of THz radiation at characteristic resonance frequencies.

H-bonds in biological macromolecules such as nucleic acids and proteins are important for their structure, biological interactions, and functions. Yet until recently there were no simple direct methods to observe and characterize H-bonds. Sub-THz vibrational spectroscopy of biological macromolecules directly targets hydrogen bonds revealing resonance spectroscopic features, vibrational modes or group of modes at close frequencies in absorption and/or transmission spectra of biomaterials. The capability of sub-THz spectroscopy to detect directly low-frequency vibrations of weak bonds between different functional groups of atoms within biological molecules is unique providing information quite different from visible or infrared spectroscopic characterization. Density of vibrational modes in the THz and especially in sub-THz regions is much lower compared to IR and far-IR, a fact that promises much higher discriminative capability of spectroscopy in this range. Indeed, THz signatures of large macromolecules are most specific to their sequence and three-dimensional structure.

Instrumentation that works in this frequency region has been limited, thus not a lot of research has been performed in this area. Till recently, Fourier transform ("FT") transmission spectroscopy (e.g., via a Bruker IFS66v instrument) provided the most detailed information on sub-THz vibrational spectral signatures of biological molecules taken with a moderate spectral resolution of approximately 0.25 cm$^{-1}$. However, the low THz power provided by traditional sources, like a mercury lamp, utilizes a detector cooled with liquid helium for reliable characterization. The approximately 12 mm optical aperture of this instrument dictated a large area sample with mg quantities of material. Measurements in air were possible since there are almost no absorption lines from water vapors or oxygen in the spectral range of approximately 10-25 cm$^{-1}$ except a water vapor absorption band at approximately 18.6 cm$^{-1}$. However, a spectral resolution of approximately 0.25 cm$^{-1}$ does not provide the required specificity of spectral features to discriminate between individual molecules or bacterial strains.

A number of instruments that are based on time domain or photomixing technologies have recently been introduced for producing and measuring THz radiation, however most of them do not have the sensitivity, or spectral and spatial resolution required for biological molecules and cells characterization.

Certain exemplary embodiments utilize a new, frequency domain, near field spectroscopic instrument with imaging capability combined with a microchip for sample material that permits characterization of traces amounts of biological materials at room temperature (see FIG. 1). This novel continuous wave, frequency domain instrument is based on a very strong local enhancement of the electromagnetic field, thus allowing increased coupling of the THz radiation with the sample biomaterials.

FIG. 1 is an exemplary sub-THz spectrometer with relatively high spectral and spatial resolution for bio-identification.

In parallel with experimental characterization, certain exemplary embodiments utilize a computational modeling technique to predict and study and better understand THz spectroscopic signatures of large macromolecules of DNAs, RNAs, proteins and other molecular components of cells using energy minimization, normal mode analysis and Molecular Dynamics approaches. Combining simulations with experimental techniques improves analysis and understanding of measured spectra and even provides predictive capabilities for modeling.

An exemplary sub-THz spectroscopic instrument has been used to measure transmission and/or absorption spectra from bio-molecules and cells and had already demonstrated very intense and narrow spectral features from biological molecules and cells with widths between approximately 0.05 and 0.15 cm$^{-1}$ that reflect low frequency molecular motions. We have found that experimental spectra from biomolecules correlate reasonably well with computational predictions, and that the spectra from different cells are sufficiently different, and that cells can be identified based on their spectral signature. Our computational modeling results confirmed that observed spectroscopic features from cells are due to fundamental physical mechanism of interaction between THz radiation and biological macromolecules inside the cell. In particular, the analysis of results indicates that the spectroscopic signatures of microorganisms originate from the combination of low frequency vibrational modes or group of modes at close frequencies (i.e., vibrational bands) within molecular components of the cells. These features were not evident in previous results obtained with a resolution of approximately 0.25 cm$^{-1}$. Multiple intense and specific resonance features provide a condition for reliable discriminative capability using sub-THz frequency domain spectroscopy, to the level of strains of the same bacteria that was not possible before.

THz vibrational spectroscopy can be used for relatively fast characterization and fingerprinting of biological molecules and organisms with limited quantities of sample materials. Even more, because biological cells are so small, sub-THz radiation propagates through the entire cell and reveals spectroscopic information from all molecular components inside the cell. Since well resolved THz spectra from biological molecules are specific to their sequence and three-dimensional structure and can be used for the fast characterization and fingerprinting of biomolecules, this method has a high potential to improve the way diagnosis of early stages of some types of cancer is conducted, offering a new optical, non-dangerous, low-cost and fast technique for identification and discrimination of cell and serum nucleic acids and proteins.

III. Materials and Methods

Cell Samples

Two human ovarian cancer cell lines, SKOV3 (ATCC® HTB-77™) and ES-2 (ATCC® CRL-1978™), were obtained from a vendor that verified their identity using genomic fingerprinting (American Type Culture Collection).

Most ovarian cancer research is based on the hypothesis that high-grade serous ovarian carcinoma ("HGSOC") arises from ovarian surface epithelial cells. Studies suggest that >approximately 50% of this lethal disease might arise from fallopian tube epithelium. Consequently it was determined useful, for comparison, to obtain sub-THz signatures from fallopian tube epithelial cells. A short-term human fallopian tube epithelial cell line (FT131) was established. All cell lines were grown in McCoy's 5A media supplemented with approximately 10% FBS. Cells were grown to confluence, trypsinized and fixed in approximately 70% ethanol, then stored frozen until analyzed. Cancer cells solutions were prepared at concentrations of approximately 150 and approximately 300 cells/0, and normal cells were prepared at approximately 100 cells/µL and approximately 50 cells/µL concentration.

Sub-THz Spectroscopy Measurements Procedure

Procedures for sub-THz spectroscopy measurements are described in detail in:

Globus T, Moyer A M, Gelmont B, Khromova T, Lvovska M I, Sizov I, Ferrance J, 2013, Highly Resolved Sub-Terahertz Vibrational Spectroscopy of Biological Macromolecules and Cells, IEEE Sens J 13 (1):72-79, doi:10.1109/JSEN.2012.2224333, which is incorporated by reference in its entirety;

T. Globus, I. Sizov, and B. Gelmont, "Terahertz vibrational spectroscopy of *E. coli* and molecular constituents: Computational modeling and experiment," Advances in Bioscience and Biotechnology, 2013, 4, 493-503, doi:10.4236/abb.2013.43A065 Published Online March 2013 (http://www.scirp.org/journal/abb/), which is incorporated by reference in its entirety; and Sizov, I., Rahman, M., Gelmont, B., Norton, M. L., & Globus, T., 2013, Sub-THz spectroscopic characterization of vibrational modes in artificially designed DNA monocrystal, Chemical Physics, 425, 121-125, doi: 10.1016/j.chemphys.2013.08.015 (http://www.scirp.org/journal/abb/), which is incorporated by reference in its entirety.

Metal microchannel arrays were fabricated from gold (approximately 3 μm thick on polymethyl methacrylate) or copper (approximately 5 μm thick on polyimide), with approximately 10 μm wide channels through the metal on approximately 150 μm centers, to serve as sample holders. A sample holder was installed into the THz spectrometer (see FIG. 1), and background frequency scans were performed at multiple locations on the array over the frequency range of the instrument (approximately 310 GHz to approximately 490 GHz). A dilute solution (suspension) of a sample was then micropipetted onto a small spot (approximately 1 mm$^2$) on the array where background scans had been performed, and allowed to dry, normally for approximately 10 minutes. Based on the size of the channels in the array and the detector opening width of approximately 200 μm, a volume of approximately 10 picoliters was interrogated in each spectroscopic measurement.

Once the sample had been applied, the detection probe was repositioned at a location previously interrogated, and the sample was scanned. Most measurements were performed where the cancer cell suspension samples had been applied but no cell was observed to be present. Since the probability of a cell being in the channel under the probe (approximately 50 μm length) is very small (less than approximately 10% in all the channels in the entire spot) and all precautions were made to not disrupt the cells, we expected that the measurements represent cell free sample spectra. Cell characterization was performed on one occasion when a cell was observed inside the channel in a location that had been previously interrogated to obtain a background spectrum. Sample transmission ("T") was calculated as the ratio of the signal spectrum (with material) to the background spectrum. Transmission was then recalculated for absorbance ("A") in relative units using $A=-\log(T)$ for analysis of scaling results depending on the amount of sample material deposited, and for further comparison with the computational modeling results.

The choice of concentration and the amount of sample material were important. As the sample holder arrays are fabricated on thin plastic substrates, too much sample introduces curvature to the substrate, significantly modifying the radiation path during sample vs. background measurements, resulting in artifacts that revealed as calculated transmission above 1. These results are not included in the analyses and required reductions in the amount of material used for measurements. An optimal concentration of cancer cell in the sample material below approximately 300 cells/μl was determined from these experiments with a sample volume of approximately 0.3-0.5 μl, since these are enough to produce a thickness after drying to receive accurate and reproducible results with rather narrow spectral features, whereas thicker dried layer lead to widening line widths due to overlapping neighboring spectral lines.

Each sample was interrogated multiple times at multiple positions on a sample holder array and at different times to demonstrate consistence spectral features, to eliminate possible artifacts and to characterize the reproducibility and sensitivity of the measurements. The reproducibility of transmission and absorption measurements is sensitive to accurate positioning of the microdetector probe in the background and sample measurements. Standard deviation values and errors for transmission have maximum values (up to 10%) at the two ends of the instrument spectral range, and at frequencies with minimum background intensities. Reproducibility of the position of spectral features on the frequency scale was better than approximately 0.1 cm$^{-1}$.

IV. Results

Ovarian carcinomas comprise a heterogeneous group of neoplasms, and there are four or five most common epithelial ovarian cancer ("EOC") subtypes, which are: high grade serous, low grade serous, endometrial, clear cell, and mucinous. Each of these histotypes has been found to be associated with mutations in specific genes and have different clinical manifestations. There are two distinct types of ovarian serous carcinoma; low grade and high grade and both are usually advanced stage (stage III or IV) at diagnosis.

SK-OV-3 and ES-2 are two epithelial histotypes. SK-OV-3 human epithelial, high grade serous carcinoma (our short notation is S-line), and ES-2 human clear cell carcinoma (our E-line), both in advanced stage (stage III or IV) at diagnosis, are the most common subtypes of ovarian carcinoma that arise from the epithelium. ES-2 human clear cell carcinomas typically present as low grade neoplasms. As a normal cell control, the FT131 cells from fallopian tubes were selected, since recent evidence suggests that greater than approximately 50% of high grade serous carcinomas in the ovary likely arise from fallopian tube epithelium tissue. The table shown in FIG. 1B lists the cancer and reference samples that were characterized.

FIG. 1B is a table of samples of cells fixed in 70% ethanol that were tested.

Since these are two ovarian cancer cell lines represented two different subtypes, we expected to see differences in their spectra. We also expect similarities for each cell line at different cell concentrations.

Figure 2A:
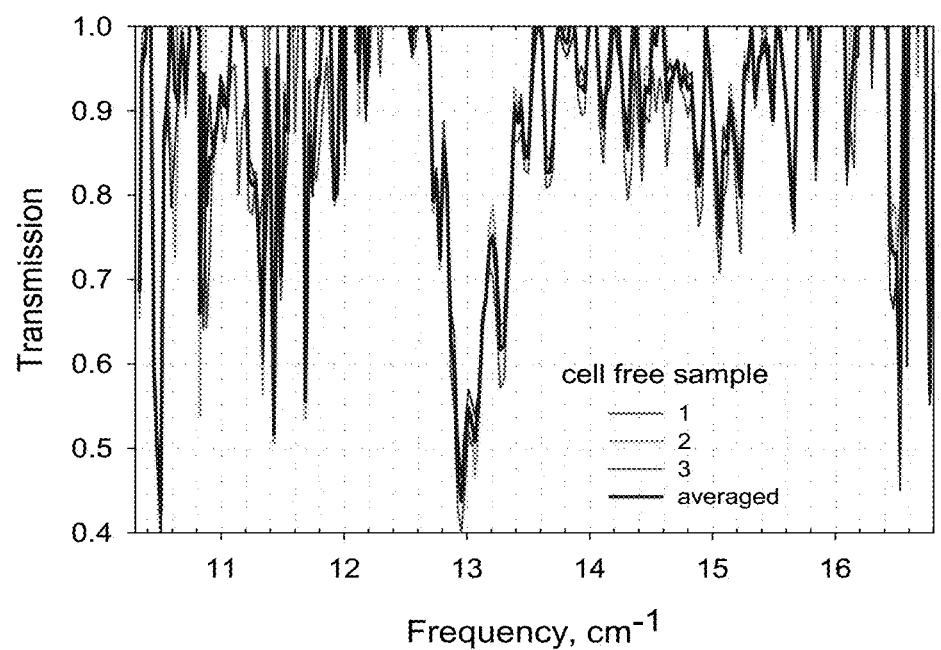
FIG. 2a an exemplary sub-THz spectral plot indicative of reproducibility of cell free, ovarian cancer ("OC") S-line sample transmission in one location with 3 different backgrounds.

FIG. 2a illustrates the spectral features in the transmission calculated for one scan of an S-line cancer cell sample with three different background measurements. In the observed results, variations are believed to have been mainly due to small mismatches in the probe position (less than approximately 1 μm) relative to the channel during the background and sample scanning. The positions of transmission sharp minima, which correspond to absorption peaks, are, however, reproduced with accuracy better than approximately 0.1 cm$^{-1}$. Absorption frequencies are the most important spectral features, and the major peak occurred at approximately 12.95+/−0.05 cm$^{-1}$ for this sample. Even for smaller peaks, the reproducibility is quite good in most cases. The intensities of lines are less important, although they generate the spectral pattern that can be used for signature analysis. The central peak in the S-line sample shows multiple relative minima, suggesting that this central feature is actually a combination of several peaks at close frequencies.

Figure 2B:
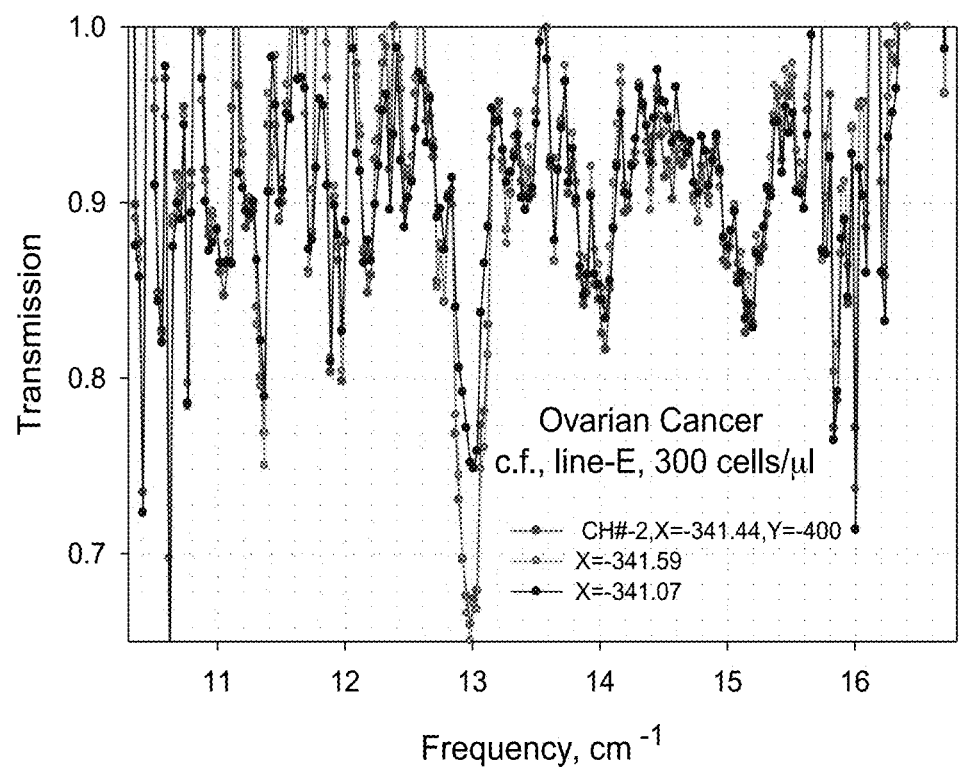
FIG. 2b an exemplary sub-THz spectral plot indicative of reproducibility of transmission spectra of a cell free OC E-line sample, 300 cells/µl, along one channel of a sample holder array.

FIG. 2b shows analysis of an E-line cancer cell sample, with sample and background measurements collected at three different positions along a channel. Once again, the frequencies of the transmission minima were reproduced almost with the same accuracy. The intensity of the absorption at each position was different, which can be explained by the different amounts of material dried at each position along the channel.

FIG. 2a is an exemplary sub-THz spectral plot indicative of reproducibility of a cell free, S-line OC sample transmission in one location with 3 different backgrounds.

FIG. 2b is an exemplary sub-THz spectral plot indicative of reproducibility of transmission spectra of cell free OC samples, E-line, approximately 300 cells/μl along one channel of a sample holder array.

Comparison of the spectra in FIGS. 2a and 2b for OC S- and E-lines demonstrate that the most intense transmission minimum, corresponding to an absorption peak, is observed at the same frequency, approximately 12.95 $cm^{-1}$. At the same time the spectral shape of this peak is simpler in the case of E-line samples and there are specific differences in spectroscopic features aside from the central peak, the most prominent are unique transmission minima at approximately 14 $cm^{-1}$, and approximately 12 $cm^{-1}$ in the E-line samples. Spectral features near both ends of the range are less reliable and will be verified in future experiments, as well as the fine structure outside the central feature.

Figure 3:
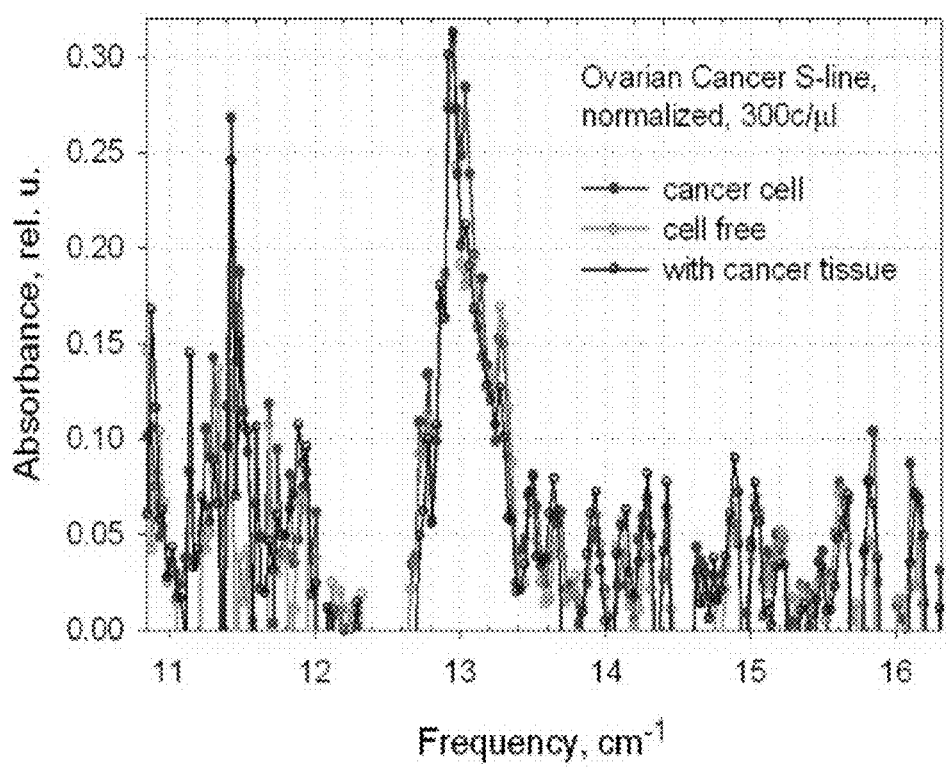
FIG. 3 an exemplary sub-THz spectral plot indicative of absorbance of S-line ovarian cancer samples (cells fixed in alcohol)

To facilitate the comparison of results from different samples for data quantification, transmission spectra were recalculated for absorbance and the spectra were normalized to the same absorbance at the peak value around approximately 13 $cm^{-1}$. When cell line samples were applied, the cells did not cover the entire area that was to be interrogated, thus spectral measurements were performed when a cell was present under the probe, when no cell was present, or in other words cell free ("c.f."), and when cell fragments were present near the probe. FIG. 3 compares the absorbance of S-line samples in cancer cell, c.f., and cell fragment regions, which all showed essentially the same spectra. We observed that the central frequency of the main absorption peak was reproduced with high accuracy of better than approximately 0.1 $cm^{-1}$. A second, rather significant absorption peak in the spectral range occurs at the frequency of approximately 11.4 $cm^{-1}$. FIG. 4 again demonstrates the similarity of absorbance features between the two cancer sample lines, S and E. Additional spectral features presented in the E-line spectra near the frequencies of approximately 11.6, approximately 12 and approximately 13.9 $cm^{-1}$ require further confirmation.

FIG. 3 an exemplary sub-THz spectral plot indicative of absorbance of S-line ovarian cancer samples (cells fixed in alcohol).

Figure 4:
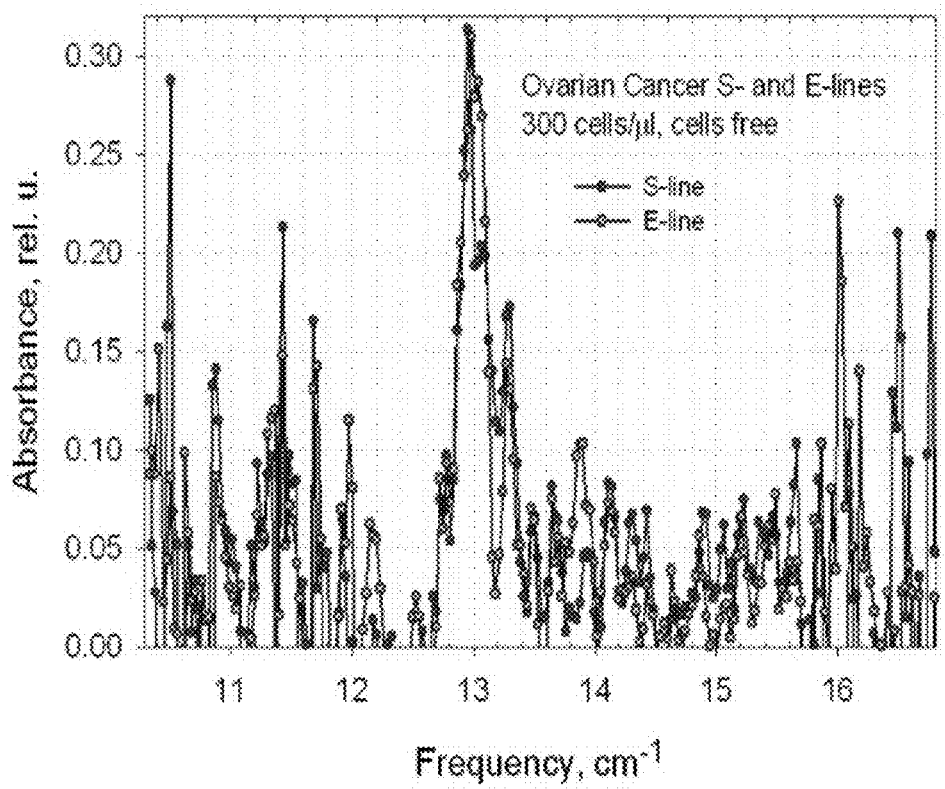
FIG. 4 an exemplary sub-THz spectral plot indicative of a comparison of absorbance spectra for two cancer cell lines, S and E.

FIG. 4 an exemplary sub-THz spectral plot indicative of a comparison absorbance spectra of two cancer lines, S and E.

Figure 5:
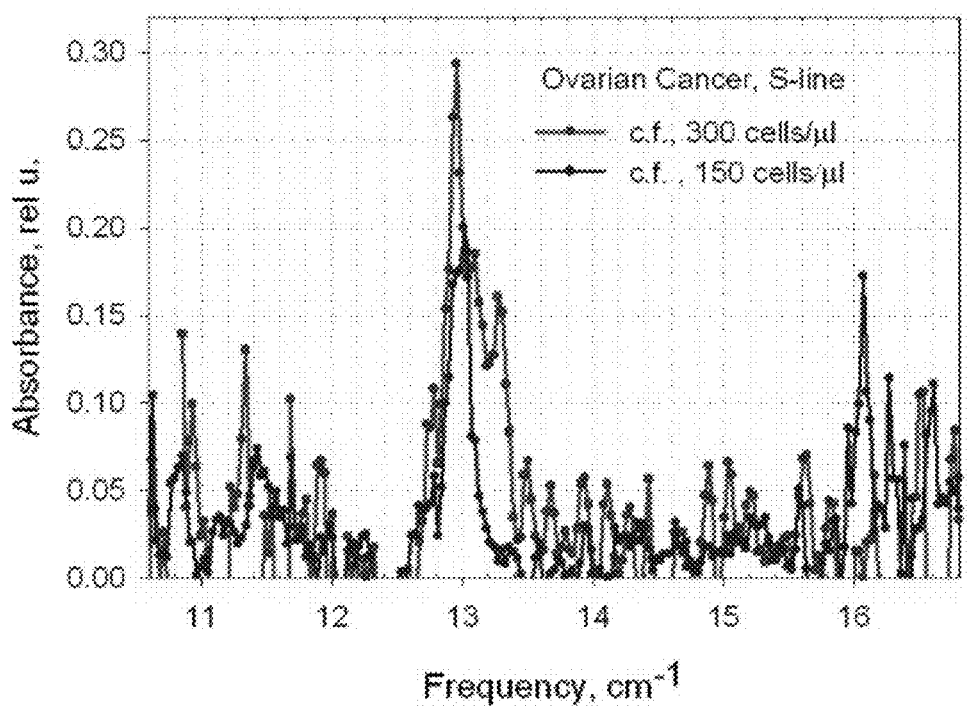
FIG. 5 an exemplary sub-THz spectral plot indicative of absorbance of OC S-line samples with concentrations of 300 and 150 cells/µl.

FIG. 5 compares absorption spectra of S-line OC samples with two concentrations of cells: approximately 300 and approximately 150 cells/W. The peak at approximately 13 $cm^{-1}$ dominates in both spectra. As we observed in many cases, samples with less amount of material very often show more narrow spectral lines. Spectroscopic signature from cancer samples is very stable and reproduces experimental results of measurements conducted in a time interval of more than approximately 2 years.

Figure 6:
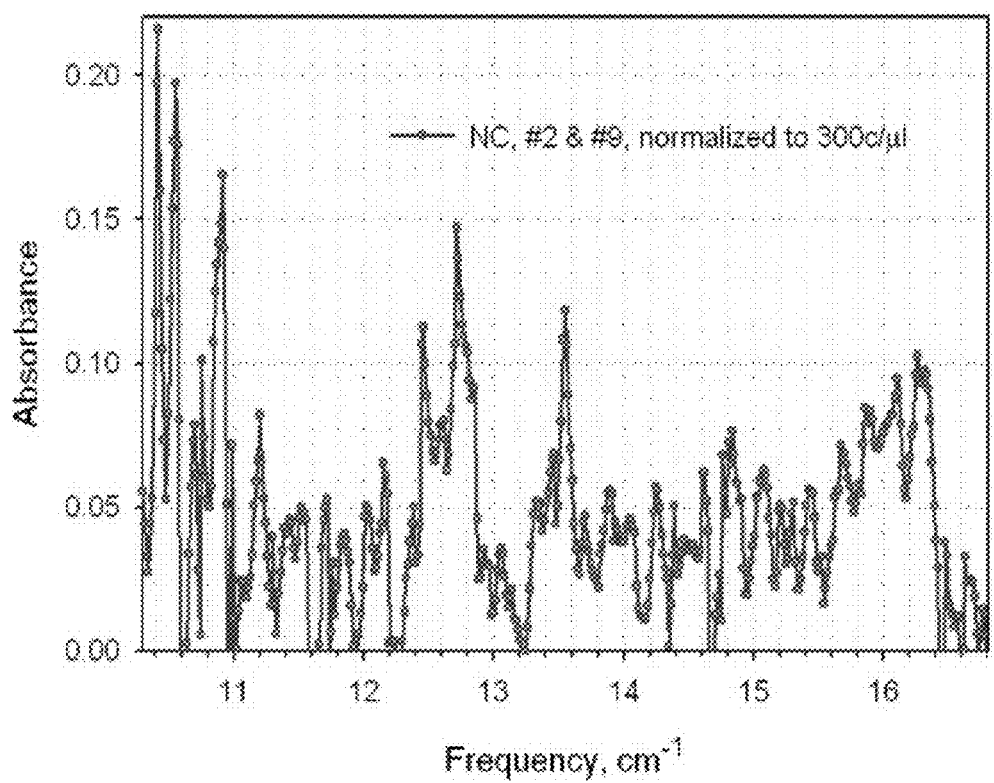
FIG. 6 an exemplary sub-THz spectral plot indicative of averaged absorbance spectrum of normal cell ("NC") samples, NC #2 and NC #9.

It is more difficult to characterize absorbance of normal cells because the spectroscopic signature is significantly weaker than that of cancer cells. FIG. 6 presents averaged result for absorbance from two normal cell samples normalized to the same concentration of approximately 300 cells/μl for convenience of comparison with cancer cell samples. Multiple absorption resonances are observed over the entire spectral range of our instrument reflecting the complex molecular content of normal cells. The pattern of the normal cell (NC) spectra seems more similar to experimental and simulated spectra of genetic (nucleic acid) molecules (i.e., DNA and/or RNA) presented in previous publications, which have been incorporated by reference, supra.

FIG. 6 an exemplary sub-THz spectral plot indicative of averaged absorbance spectrum of normal cell samples, NC #2 and NC #9.

The result shown in FIG. 6 is the first and an important demonstration of the sub-THz spectroscopic signature from fallopian tube epithelium cells. If these cells may indeed be the origin for high-grade serous ovarian carcinoma, the modification of this signature might become the first sign of ovarian cancer at the initial step of disease development that can be used for early cancer detection and diagnosis.

Figure 7A:
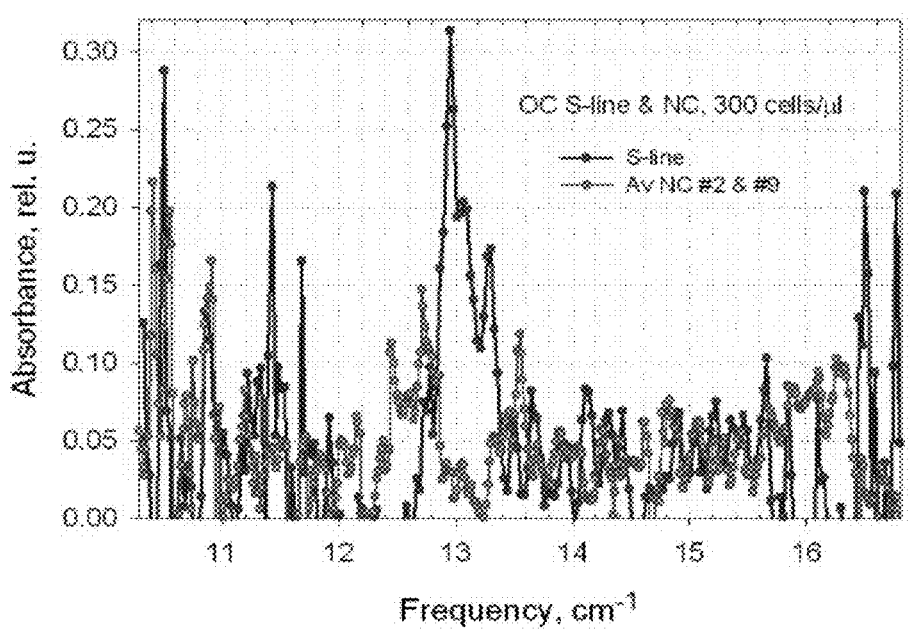
FIG. 7A an exemplary sub-THz spectral plot indicative of absorbance of OC S-line & NC #2 & 9 samples.
Figure 7B:
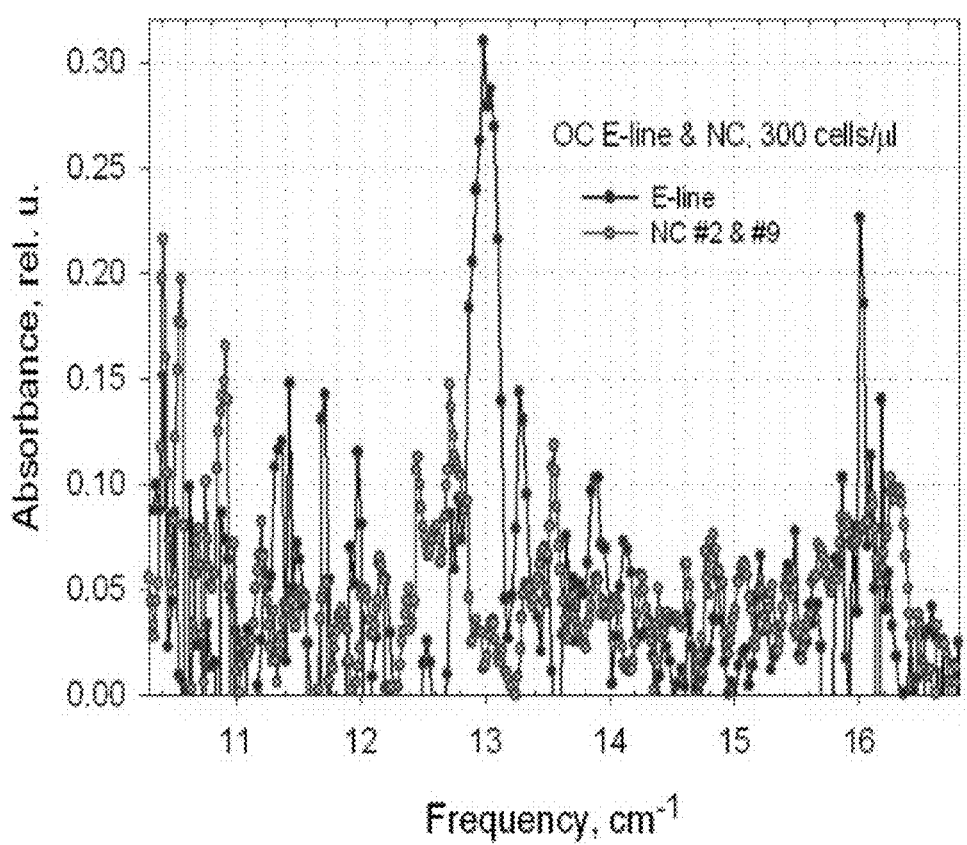
FIG. 7B an exemplary sub-THz spectral plot indicative of absorbance of OC E-line & NC #2 & 9 samples.

FIGS. 7A and 7B compare directly the absorbance of the ovarian cancer S-line and E line cells with normalized spectra of normal cells. Beyond the central peak at approximately 13 $cm^{-1}$ attributed to OC, there is some similarity between the CC and NC that seems slightly more correlated for the S-line at frequencies of approximately 10.5 $cm^{-1}$, approximately 10.9 $cm^{-1}$, approximately 14.3 $cm^{-1}$, and approximately 15.7 $cm^{-1}$, while for E-line at frequencies of approximately 12.2 $cm^{-1}$ and approximately 15.9-16.2 $cm^{-1}$. However, these portions of the spectra do not necessary have to correlate, as different proteins, contributing to absorption in this region, are expected to be present in the different cell types.

FIG. 7A an exemplary sub-THz spectral plot indicative of absorbance of CC S-line & NC #2 & 9.

FIG. 7B an exemplary sub-THz spectral plot indicative of absorbance of CC E-line & NC #2 & 9.

V. Molecular Dynamics Simulations.

We observed a dramatic difference between the THz absorption spectra of cancer and normal cells with much higher intensity and a very strong peak at a frequency of approximately 13 $cm^{-1}$, which dominated the spectra from cancer samples in the spectral range of the instrument used. Neither DNA nor protein molecules have a spectral transmission/absorption pattern in this spectral range that shows any significant correlation with the experimental results from cancer cells demonstrated in FIGS. 2a, 2b, 3-6, 7a, 7b, and 9. The signatures of the protein thioredoxin and DNA from E. coli can be found in previous publications; incorporated by reference, supra; for comparison. At the same time, results from medical literature search discussed in the Section VI suggest that one potential source of this strong and specific spectral feature in cancer samples could be short double stranded molecules of matured miRNAs.

To verify whether the contribution from miRNAs can explain the observed cancer signature, we conducted molecular dynamics simulation to predict the sub-THz absorption signatures from specific miRNAs that were studied in the literature and were shown to be the most overexpressed and important in ovarian cancer. The high overexpression level of miR-200 family and the involvement of these molecules in epithelial OC as well as other cancers were determined in many studies. The miRNA-200 family comprises miR-200a, 200b, 200c, and miR-141. The sequences of these miRNAs found in http://www.mirbase.org using entries as indicated, are shown below in FIG. 7C, which is a table of studied miRNAs.

FIG. 7C is a table of studied miRNAs.

In normal cells miRNA regulates formation of mRNA. The short noncoding regulatory RNAs are derived from regions of RNA transcripts that fold back on themselves to form short hairpins. In the maturation process, the single strands of miRNAs find complimentary part of mRNAs. During posttranslational regulation the hairpin is cleaved, which is followed by formation of an imperfect miRNA duplex about 22 nucleotides in length. Mismatch defects in this duplex occur when the complementary pair can not be created. Thus, during maturation, microRNA forms a duplex, whose three dimensional structure can be reconstructed using a molecular dynamics software such as MacroMoleculeBuilder and/or Assemble2, etc.

Two-dimensional drawings showing imperfect structures of the molecules for simulation without loop but with mismatches are presented in FIGS. 8A, 8B, and 8C.

FIGS. 8A, 8B, and 8C show human miRNA duplex models, mir-200a, 200b and 200c after maturation (without loop but with mismatches). Each circle represents a base (residue). Bases connected with vertical lines correspond to complimentary pairs.

Molecular dynamics protocol and absorption coefficient calculation are described previously in Alijabbari, N., Chen, Y., Sizov, I., Globus, T., & Gelmont, B., 2012, Molecular dynamics modeling of the sub-THz vibrational absorption of thioredoxin from *E. coli*. Journal of Molecular Modeling, 18(5), 2209-2218. doi:10.1007/s00894-011-1238-6. PMID: 21947449; which is incorporated by reference herein in its entirety. Initial atomic coordinates of miRNAs were found using data available in the mirbase.org database in a Vienna format. The data were downloaded into Assemble2 software, where atomic coordinates were then restored for the chain that has a 3'5' direction and the complimentary chain in 5'3' direction.

Figure 9:
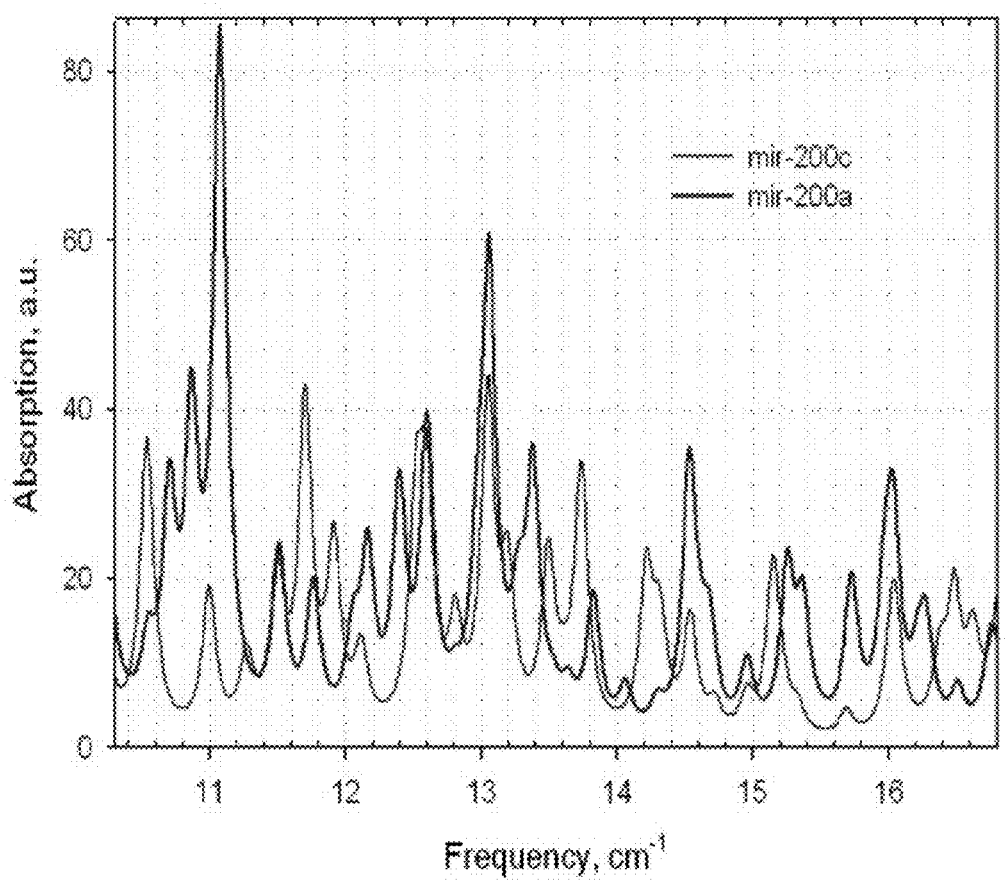
FIG. 9 an exemplary simulated sub-THz spectral plot indicative of absorption signatures of miR-200a and 200c with mismatches, showing that both have strong absorption peaks at approximately 13 cm$^{-1}$.
Figure 10:
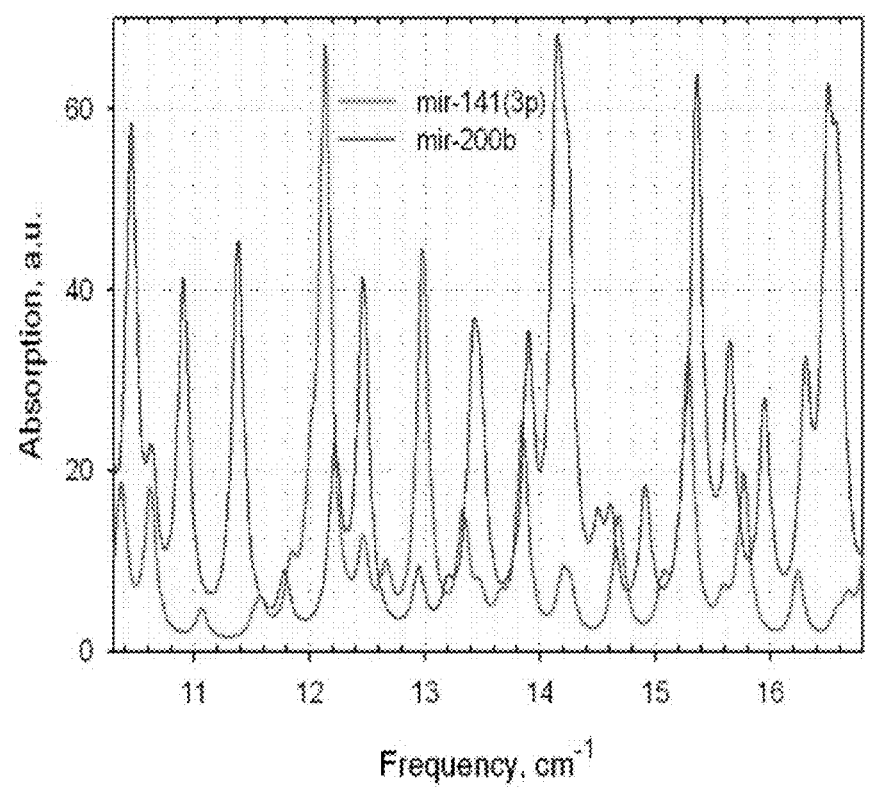
FIG. 10 an exemplary simulated sub-THz spectral plot indicative of absorption signatures of miR-200b with mismatches and miR-141 (3p ideal) that also shows a strong peak at approximately 13 cm$^{-1}$.

Sub-THz absorption spectra were calculated using the MD simulation for four members of the miR-200 family, including miR-141, and are presented in FIGS. 9 and 10. Spectra from three of these four molecules (miR-200a, miR-200c and miR-141) show a significant absorption peak at approximately 13 cm$^{-1}$ along with additional absorption peaks at other frequencies. As expected, the spectra from each of these individual miRNAs are unique. However, none of them looks similar to the experimental result for cancer cell material.

FIG. 9 an exemplary sub-THz spectral plot indicative of absorption signatures of mir-200a and 200c with mismatches that both have strong absorption peaks at approximately 13 cm$^{-1}$.

FIG. 10 an exemplary sub-THz spectral plot indicative of absorption signatures of mir-200b with mismatches and mir-141 (3p ideal), which also shows a strong peak at approximately 13 cm$^{-1}$.

VI. Discussion.

In cancer cells specific miRNA molecules can become deregulated showing increased concentrations in blood, serum and tissue cells. Since miRNAs modulate the expression of critical genes and the signaling networks involved in tumorigenesis, there is mounting evidence that miRNAs are involved in cancer development. According to experimental studies, miRNAs can be overexpressed by approximately 20-600 times during cancer progression. MiRNAs are present in ovarian cancer (OC) cell-free bodily fluids, and these molecules are the major fraction of small nucleotide species in serum. MiRNAs in serum are sufficiently stable to serve as clinical biomarkers, serum mRNA profiles reflect physiological conditions, and circulating miRNAs are correlated with tumor progression. All these facts can explain the difference in sub-THz absorption spectra of cancer and normal cell samples observed in our measurements.

The choice of specific miRNA for analysis of spectroscopic signatures is also important since the human genome encodes approximately 550 miRNA genes to express about 1,000 miRNAs. However, these miRNAs are found to be differentially expressed in various human cancer cell types. For example it was shown that only approximately 4 of 29 miRNAs, miR-141, miR-200a, miR-200b, and miR-200c, were upregulated in one study. The miR-200 family among other mi-RNAs is upregulated 50-100 times over normal expression levels in endometrioid ovarian cancer compared to normal primary human ovarian surface epithelium (HOSE) culture. A gene network has been identified along with the predicted regulatory miRNAs that characterized a phenotype of serous epithelial ovarian cancer (EOC). This showed that approximately 89% of the target genes in the network were regulated by 8 key miRNAs. Two of these key miRNAs, miR-141 and miR-200a, are members of the miR-200 family.

The high overexpression level of miR-200 family was also determined in other studies: the miRNA-200 family has repeatedly been implicated for its involvement in EOC as well as other cancers. In addition, miRNA signatures are different between ovarian carcinoma histotypes (serous, endometrioid, clear cell, and mucinous), which could account for the differences we observed in the experimental spectra of the S and E line cells.

The involvement of the miRNA-200 family (miR-200a, 200b, 200c, miR-141) and miR-429 in epithelial OC as well as other cancers has been determined in additional studies. The major findings show changes in concentrations of miR-200a, 141, 200c and 200b. MiR-200a and miR-200c showed increased expression in serous, endometrioid and clear cell cancer while miR-200b and miR-141 were up-regulated in endometrioid and serous histotypes thereby indicating histotype specificity. It was found that only miR-200c and 141 were upregulated in high-grade serous tumors.

Expression levels of serum miRNAs are reproducible and consistent among individuals. At the same time, many regulating proteins, which experience upfold changes during cancer development and thus can be considered as potential contributors to absorption difference between cancer and normal cells, are found to have overexpression level of approximately 5-10 times. This is not high enough overexpression to account for the large absorption peak observed in our measurements for cancer cell samples.

We have earlier demonstrated that short DNA duplexes have strong specific symmetry vibrational resonances in the sub-THz frequency range. It was shown that the internal low-frequency motions correspond to helical twisting, bending, and stretching, and sugar pseudo rotational vibrations. These motions and absorption spectra are affected by DNA length, nucleotide composition, and topology (A-, B- or Z-form). These strong spectral features can explain the central spectral peaks presented in FIGS. 5-9. The rest of the cancer signature shown in these figures is in part similar to the signatures of normal cells and most probably represent contribution from proteins and other molecules that might carry genetic information.

Figure 11:
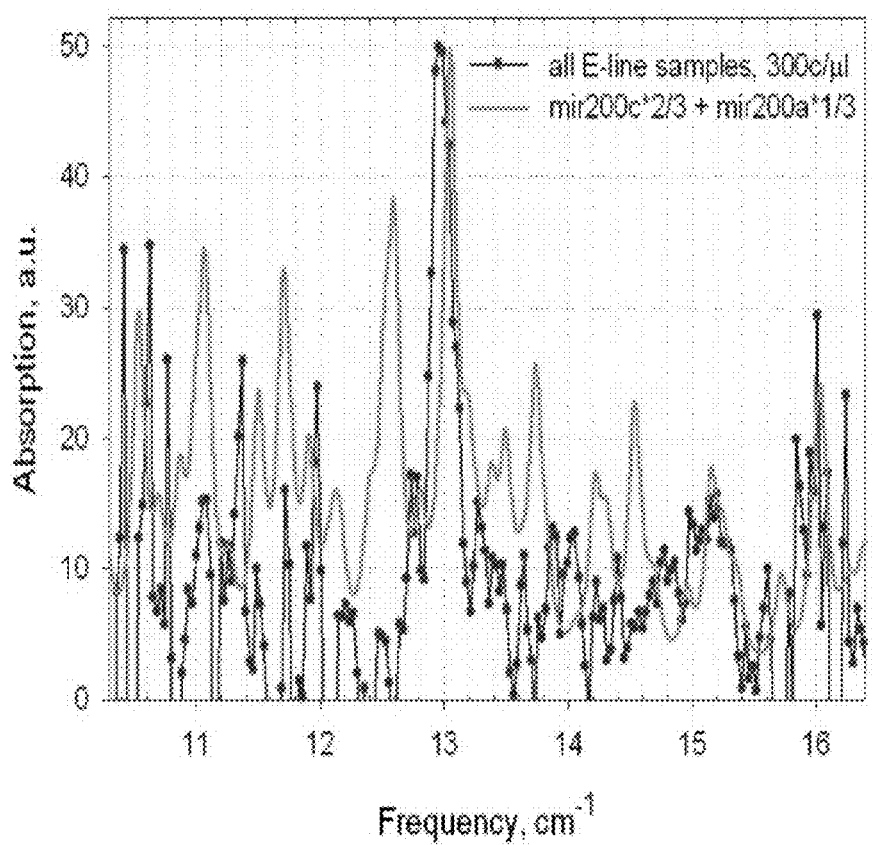
FIG. 11 are exemplary sub-THz spectral plots showing a comparison of measured sub-THz absorption spectra averaged over all E-line samples, 300 cells/µl, with modeled spectra for a miR-200c and miR-200a mixture.
Figure 12:
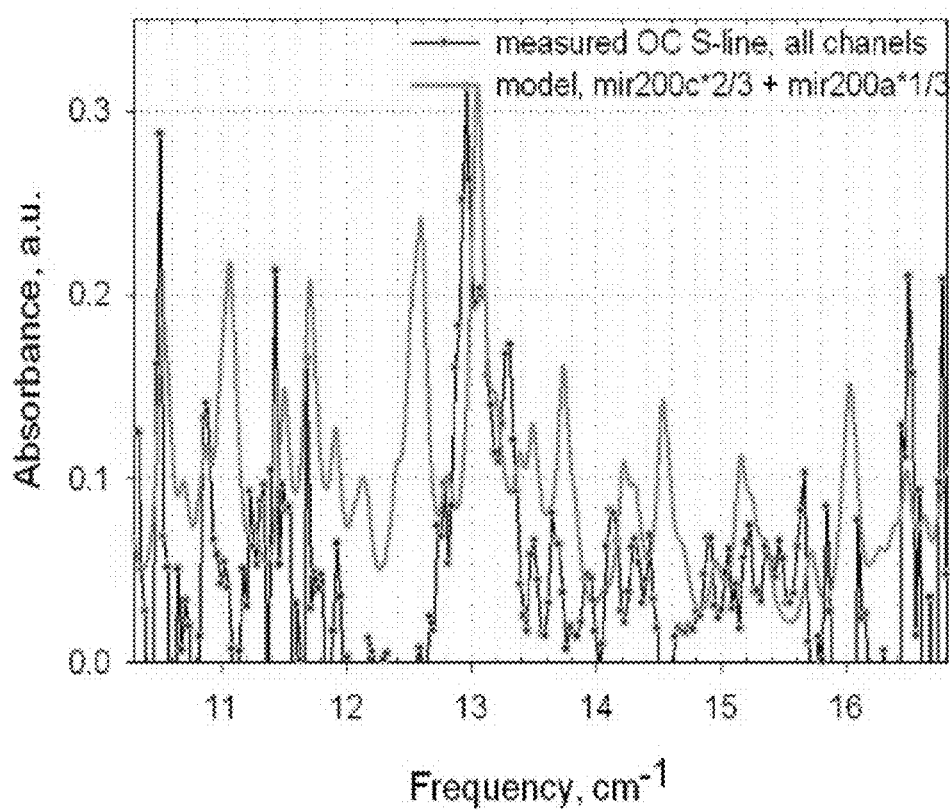
FIG. 12 are exemplary sub-THz spectral plots showing a comparison of measured sub-THz absorption spectra averaged over S-line samples, 300 cells/µl, with modeling for a miR-200c and miR-200a mixture.

Both, miR-200a and miR-200c show increased expression in serous, endometrioid and clear cell cancers. The S line of cancer cells (SKOV3) represents a high-grade serous type tumor, and the E-line cells (ES2) represent a clear cell carcinoma. For this reason we compared in FIGS. 11 and 12 the experimental absorbance spectra from an E-line and from S-line cancer samples, correspondingly, with the simulated signatures from a mixture of mir-200a and 200c, however in different proportions. While the simulation from neither of these individual miRNAs had the largest peak at approximately 13 cm$^{-1}$, the additive effects of the simulation mixture at this frequency makes this peak stand out above other peaks in the spectra. Correlations of many features in the simulated mixture and the experimental spectra of both lines shown in FIGS. 11 and 12 are obvious. The most significant disagreement is observed at frequencies of approximately 12.6, approximately 13.7 and approximately 14.5 cm$^{-1}$. This can be understood because the real situation is much more complicated and the contribution from other miRNAs including miR-141 and miR-200b, as well as other possible overexpressed molecules cannot be eliminated.

In addition to the presence of other miRNAs and other overexpressed biomolecules, there are other possible reasons for the partial disagreement between experimental and simulated spectra. In particular, since there is currently no understanding of what the 3D structure of miRNAs actually is when they are released from the cells such as in exosomes containing these circulating molecules in blood, the simulation represented our best understanding of the miRNA structures at this point.

FIG. 11 are exemplary sub-THz spectral plots showing a comparison of measured sub-THz absorption spectra averaged over all E-line samples, 300 cells/µl, with modeling for a miR-200c and miR-200a mixture.

FIG. 12 are exemplary sub-THz spectral plots showing a comparison of measured sub-THz absorption spectra averaged over S-line samples in all channels, 300 cells/µl, with modeling for a miR-200c and miR-200a mixture.

An exemplary embodiment was utilized to perform what is believed to be the very first study on the results for spectroscopic signatures from cell lines representing endometrial ovarian cancer in the sub-THz frequency range. It is already easy to observe major differences between cancer and normal samples in this spectral range that might allow for use of this method as a new cancer diagnostic technique. Correlation of the signature change with tumor progression needs to be studied, and a more thorough investigation and detailed analysis can be used to understand the observed variability of absorption peak intensities. For example, the scalability of peak intensities does not follow Beer's law at some frequencies, and increased intensity of the central peak is often observed in the thinnest samples, less than approximately 1 µm.

Conclusions

Certain exemplary embodiments provide for the application of sub-THz absorption/transmission technology for early cancer diagnostic and prognosis, which can be simpler than current methods. Since THz radiation detects signatures from components inside the cancer cells, the complicated procedures of extracting biomarkers from the cells can be eliminated. This spectroscopic method provides the opportunity to look for specific spectral signatures from molecules within each cell, to differentiate between cell types, or to look at influences of environmental factors on cellular function, representing new analytical research capabilities not provided by previous instrumentation. The new technology would be applicable for a) laboratory testing of unique spectroscopic signatures from markers like DNA, RNA, and protein biomarkers, or from entire cells in specimens from core or fine-needle aspiration biopsies from most types of cancer, b) spectroscopic evaluation of potential molecular markers in saliva or blood (for example, circulating short RNA molecules) in conjunction with standard molecular biology techniques. The new technology can also significantly assist quantitative PCR ("qPCR") methods by providing quick preliminary data and making DNA and RNA analysis a more effective and targeted procedure.

Figure 13:
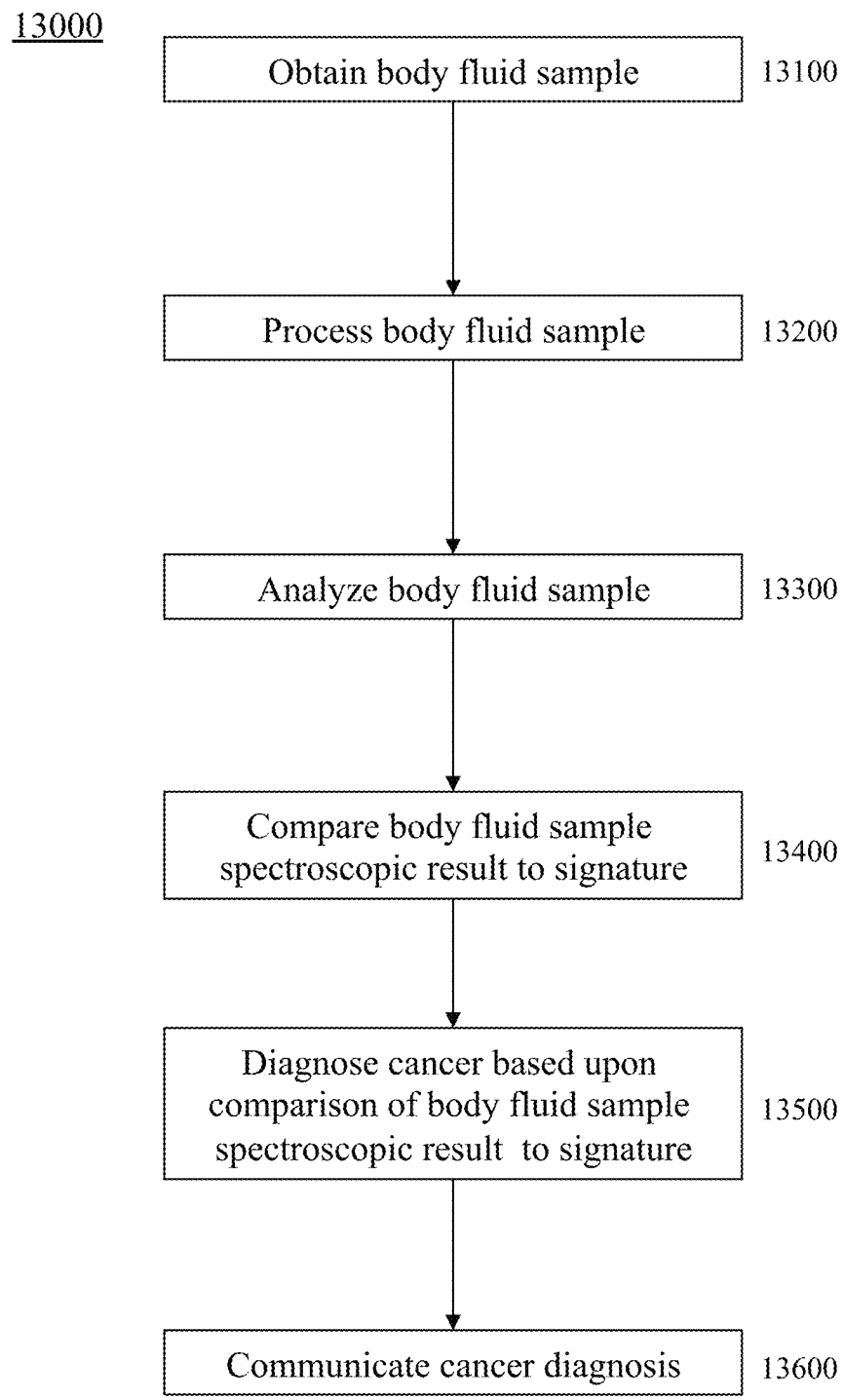
FIG. 13 is a flowchart of an exemplary embodiment of a method 13000.

FIG. 13 is a flowchart of an exemplary embodiment of a method 13000. At activity 13100, a body fluid sample can be obtained and/or caused to be obtained. The body fluid sample can comprise at least one of plasma, blood, lymph, saliva, urine, stomach acid, or tears. The body fluid sample can comprise an alcohol-water mixture extract from cancer cells.

At activity 13200, the body fluid sample can be processed and/or caused to be processed. At activity 13300, the body fluid sample can be analyzed via terahertz spectroscopy. The sub-THz resonance spectroscopy of the body fluid sample can result in multiple absorption peaks at frequencies between 0.05 and 1.0 THz. At activity 13400, the spectroscopic result can be compared to a predetermined and/or pre-analyzed signature. For example, a molecular dynamics and normal mode analysis computation can be utilized to predict spectroscopic absorptions between 0.05 and 1.0 THz for cancerous body fluids.

At activity 13500, a cancer diagnosis can be made based upon the comparison of the body fluid sample spectroscopic result to the pre-analyzed signature. Certain exemplary embodiments cause a determination to be made that a body fluid sample is from a patient with cancer. The determination can be made via analyzing the body fluid sample by sub-THz resonance spectroscopy with absorption determinations being made at a plurality of frequencies between 0.05 and 1.0 THz to show the presence of specific Micro-RNAs as cancer related molecules in the body fluid. Certain exemplary embodiments can automatically determine a probability that the patient has cancer via a comparison of the spectroscopy results of the body fluid sample to predicted results for cancerous body fluids.

In certain exemplary embodiments, an automatic determination can be made that the patient has cancer via a comparison of the spectroscopy results of the body fluid sample to previous experimental results for cancerous body fluids.

Cancer cells analyzed can comprise at least one of ovarian cancer, breast cancer, cervical cancer, head and neck cancers in non-smoking patients.

At activity 13600, the cancer diagnosis can be communicated with a medical professional and/or the patient from whom the body fluid sample was taken.

DEFINITIONS

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

absorption—the manner in which the energy of a photon is taken up by matter, causing motion (bending, stretching, rotation, vibration, etc.) in molecules or atoms, or transitions between energy levels by the electrons of an atom.

activity—an action, act, step, and/or process or portion thereof adapter—a device used to effect operative compatibility between different parts of one or more pieces of an apparatus or system.

analyze—to evaluate.

and/or—either in conjunction with or in alternative to.

apparatus—an appliance or device for a particular purpose associate—to join, connect together, and/or relate.

body fluid sample—a liquid specimen originating from inside of a body of a living person, which can comprise, for example, a liquid that is excreted or secreted from the body of the living person.

can—is capable of, in at least some embodiments.

cancer—one or more of a group of diseases involving abnormal cell growth with the potential to invade or spread to other parts of the body.

cause—to produce an effect.

circuit—an electrically conductive pathway and/or a communications connection established across two or more switching devices comprised by a network and between corresponding end systems connected to, but not comprised by the network.

comprising—including but not limited to.

configure—to make suitable or fit for a specific use or situation.

connect—to join or fasten together.

constructed to—made to and/or designed to.

convert—to transform, adapt, and/or change.

coupleable—capable of being joined, connected, and/or linked together.

coupling—linking in some fashion.

create—to bring into being.

define—to establish the outline, form, or structure of determine—to obtain, calculate, decide, deduce, and/or ascertain.

device—a machine, manufacture, and/or collection thereof constructed for a given purpose.

estimate—to calculate and/or determine approximately and/or tentatively.

frequency—a count of cycles of radiation waves per unit time.

generate—to create, produce, give rise to, and/or bring into existence.

initialize—to prepare something for use and/or some future event.

install—to connect or set in position and prepare for use.

may—is allowed and/or permitted to, in at least some embodiments.

method—a process, procedure, and/or collection of related activities for accomplishing something.

mir-200—in molecular biology mir-200 microRNA is a short RNA molecule; microRNAs function to regulate the expression levels of other genes by binding and cleaving mRNAs or inhibiting translation.

miR-200 family—short RNA molecules comprising miR-200a, miR-200b, miR-200c, miR-141, and miR-429; there are growing evidences to suggest that miR-200 microRNAs are involved in cancer metastasis.

mkm—a unit for measuring length (1 mkm=$10^{-6}$ m=1000 nm).

molecular dynamics computation—a computer simulation that studies the physical movements of atoms and molecules and predicts sub-THz absorption spectra of molecules.

patient—a human or other type of animal under supervision for health care purposes.

PCR—polymerase chain reaction.

peak—an apex observed in a spectral graph.

plasma—fluid component of blood.

plurality—the state of being plural and/or more than one.

predetermined—established in advance.

predict results—to estimate an actual spectra based upon physical and chemical characteristics.

probability—a quantitative representation of a likelihood of an occurrence.

project—to calculate, estimate, or predict.

provide—to furnish, supply, give, and/or make available.

radiation—the emission or transmission of energy waves through space or through a material medium.

receive—to get as a signal, take, acquire, and/or obtain.

recommend—to suggest, praise, commend, and/or endorse.

render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

request—to express a desire for and/or ask for.

select—to make a choice or selection from alternatives.

serum—a fraction of blood from which the cells and clotting factors have been removed set—a related plurality.

store—to place, hold, and/or retain data, typically in a memory.

substantially—to a great extent or degree.

sub-THz resonance spectroscopy—an analytic method wherein electromagnetic radiation is applied to a sample over a range of frequencies that is less than one THz, wherein the method measures absorptions by a sample material over the range of frequencies, which absorptions can then be expressed in a graphical output.

support—to bear the weight of, especially from below.

system—a collection of mechanisms, devices, machines, articles of manufacture, processes, data, and/or instructions, the collection designed to perform one or more specific functions.

TaqMan assay—nucleic acid analysis method that utilizes a quantitative polymerase chain reaction process.

transmit—to send as a signal, provide, furnish, and/or supply.

via—by way of and/or utilizing.

weight—a value indicative of importance.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

no characteristic, function, activity, or element is "essential";

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope. No claim of this application is intended to invoke paragraph six of 35 USC 112 unless the precise phrase "means for" is followed by a gerund.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

What is claimed is:

1. A method comprising:
via a sub-THz spectrometer, obtaining data used in a determination that a body fluid sample is from a patient with cancer, the determination made via analyzing the body fluid sample by sub-THz resonance spectroscopy with absorption determinations being made at a plurality of frequencies between 0.05 and 1.0 THz to show a presence of specific Micro-RNAs as cancer related molecules in the body fluid.

2. The method of claim 1, further comprising:
automatically determining that the patient has cancer via a comparison of the spectroscopy results of the body fluid sample to previous experimental results for cancerous body fluids.

3. The method of claim 1, further comprising:
automatically determining a probability that the patient with cancer has cancer via a comparison of the spectroscopy results of the body fluid sample to predicted results for cancerous body fluids.

4. The method of claim 1, wherein:
a molecular dynamics and normal mode analysis computation predicts spectroscopic absorptions between 0.05 and 1.0 THz for cancerous body fluids.

5. The method of claim 1, wherein:
the sub-THz resonance spectroscopy of the body fluid sample results in multiple absorption peaks at frequencies between 0.05 and 1.0 THz.

6. The method of claim 1, wherein:
the body fluid sample comprises at least one of plasma, blood, lymph, saliva, urine, stomach acid, or tears.

7. The method of claim 1, wherein:
the body fluid sample comprises an alcohol-water mixture extracted from cancerous cells.

8. The method of claim 1, wherein:
cancer cells comprise at least one of ovarian cancer, breast cancer, cervical cancer, and head or neck cancers in non-smoking patients.

9. A method comprising:
creating a sub-THz spectrometer system constructed to determine that a body fluid sample is from a patient with cancer, the determination made via analyzing the body fluid sample by sub-THz resonance spectroscopy with absorption determinations being made at a plurality of frequencies between 0.05 and 1.0 THz to show a presence of specific Micro-RNAs as cancer related molecules in the body fluid.

* * * * *